United States Patent [19]

Morris

[11] Patent Number: 5,288,492

[45] Date of Patent: Feb. 22, 1994

[54] DECONGESTANT COMPOSITION CONTAINING ALOE VERA

[76] Inventor: Michael A. Morris, Rte. 1 Box 89A, Church Hill, Md. 21623

[21] Appl. No.: 975,716

[22] Filed: Nov. 13, 1992

[51] Int. Cl.⁵ ............... A61K 35/78; A61K 31/20
[52] U.S. Cl. ..................... 424/195.1; 424/678; 424/722; 514/558
[58] Field of Search ............ 424/195.1, 678, 722; 514/558

[56] References Cited

U.S. PATENT DOCUMENTS

| | | | |
|---|---|---|---|
| 4,725,438 | 2/1988 | Leazer | 424/195.1 |
| 4,826,683 | 5/1989 | Bates | 424/641 |
| 4,857,328 | 8/1989 | Trenzelok | 424/195.1 |

*Primary Examiner*—John W. Rollins
*Attorney, Agent, or Firm*—Richard C. Litman

[57] ABSTRACT

A decongestant composition and method are provided for treatment of symptoms associated with respiratory disorders. The composition in the form of an aqueous solution which comprises aloe vera, castor oil, sodium metasilicate and calcium chloride as the essential active components. The decongestant can be topically applied to the nasal or bronchial passages from dispensers containing spray means or inhalation mist means.

8 Claims, No Drawings

DECONGESTANT COMPOSITION CONTAINING ALOE VERA

BACKGROUND OF THE INVENTION

1. Field of the Invention

This invention relates to a decongestant composition for treatment of symptoms associated with respiratory disorders. More particularly, the invention pertains to an aqueous decongestant spray composition containing aloe vera extract for topical administration to nasal or bronchial passages.

2. Description of the Prior Art

There are a number of decongestant formulations on the market today which have been found to be temporarily effective in relieving one or more symptoms associated with respiratory diseases. Such symptoms include nasal congestion, runny and itchy nose, sneezing, itchy and watery eyes, cough, bronchoconstriction and post-nasal drip. These symptoms are generally associated with respiratory disorders such as colds, allergic rhinitis, asthma, sinusitis, and bronchitis. An example of a nonprescription decongestant is a nasal spray containing a 0.1% aqueous solution of xylometazoline hydrochloride as the active ingredient and is available under the trade name Sinex Long-Acting from Vicks Health Care. This product constricts the arterioles of the nasal passages to temporarily restore freer breathing and helps decongest sinus openings and passages to promote sinus drainage. However, periodic relief is often achieved with accompanying side effects, such as drowsiness, CNS depression or rebound congestion. Also, it is recommended that this product not be used for more than three days since its use in excess of the recommended dosage may cause burning, sneezing or increase in nasal discharge.

U.S. Pat. No. 4,826,683 to Bates discloses a decongestant nasal spray comprising vegetable oil, aloe vera, a therapeutic compound of zinc, and vitamins as the active components. While this nasal decongestant preparation is characterized as being non-irritating to nasal passages, it contains separable phases and must be shaken prior to use to insure that the preparation is homogeneous. In addition, the disclosed preparation offers no treatment for lower respiratory symptoms, such as bronchoconstriction and cough.

SUMMARY OF THE INVENTION

It is, accordingly, a primary object of the present invention to provide a safe and effective decongestant composition for the treatment of symptoms associated with respiratory diseases.

It is a further object of the invention to provide a decongestant composition for the treatment of upper respiratory nasal symptoms, as well as lower respiratory symptoms.

It is among the additional objects of the present invention to provide a decongestant formulation in a dispenser comprising spray means for topical application of the decongestant to the nasal or bronchial passages.

These and other objects are accomplished in accordance with the present invention which provides a decongestant composition in the form of an aqueous solution comprising aloe vera, castor oil, sodium metasilicate and calcium chloride as the essential active components. The combination of specific active components are formulated in such relative proportions as to bring about a decongestant effect, whereby topical administration of the compositions to the nasal or bronchial passage according the method of the present invention produces a marked therapeutic result, as well as a moisturizing effect on breathing passages.

A preferred mode of administering the above compositions by the method of the present invention is topical, intranasal administration, e.g., with nasal spray or nasal mist inhalation. Another preferred mode of administering the present compositions is topical, bronchial administration from a container by inhalation of the therapeutic mist. Such modes of administration prevents any gastro-intestinal effects of the compositions.

The foregoing and other features, advantages and other objects of the invention may be more fully appreciated by reference to the following detailed description.

DETAILED DESCRIPTION OF THE INVENTION

In accordance with the preferred embodiments of the present invention, I have surprisingly discovered that a safe and effective decongestant may be formulated by combining 20 to 35% by weight of aloe vera, 5-15% castor oil, 5-10% sodium metasilicate, 5-10% and calcium chloride as the active ingredients with 30 to 65% by weight of purified water to form an aqueous solution.

In preparing the present compositions, the liquid latex (exudate) or clear gel(mucilage) of the aloe vera plant may be used. Aloe vera gel, the mucilaginous jelly from the parenchyma cells of the plant, is preferred and fresh gels of the aloe plant are most preferred. Also, it is preferred to use purified water in which the ions have been removed since deionized water serves as a more efficient solvent or carrier for the active ingredients.

The preparation of the compositions of the present invention may be achieved economically and rapidly. Preferably, the castor oil, sodium metasilicate, and calcium chloride in the designated proportions are intermixed with a less than total quantity of water by suitable agitation, as by a standard mixer. The aloe component of the composition is then added to the intermixture with continued agitation and the resulting mixture diluted with the remaining amount of water while stirring to form an aqueous solution. The solution formation may be accelerated by subjecting the mixture of ingredients to heat, within the range of approximately 50° C. to 60° C., with attendant stirring. However, it should be understood that the composition ingredients will present an homogeneous appearance with agitation under ambient conditions without the need for heating.

The present invention involves the use of a safe and effective amount of the above compositions for treatment of symptoms associated with respiratory diseases of especially humans. The respiratory diseases may include colds, flu, allergic and vasomotor rhinitis, asthma, sinusitis, and bronchitis. Symptoms associated with these diseases include, for example, nasal congestion, runny nose, sneezing, itchy nose, itchy eyes, watery eyes, cough, bronchoconstriction and post-nasal drip.

The compositions of the present invention particularly provides for the treatment of upper respiratory nasal symptoms and also lower respiratory symptoms such as bronchoconstriction and cough. Preferred compositions for topical administration to the nasal passages and sinuses include nasal sprays and/or mists for nasal inhalation. Preferred compositions for topical administration to the bronchial passages and lungs include mouth inhalation.

Relief of the above symptoms can be safely and effectively achieved with no side effects Which often accompany other therapies. The terminology "safe and effective amount" as used herein denotes an amount of the present compositions sufficiently high enough to provide beneficial modification of the condition to be treated, but low enough to avoid any undesirable side effects. Based on actual experience, the present decongestant sprays have been found to be unexpectedly effective and there has been no reported incidence of any irritation to breathing passages or any significant risk to health.

A safe and effective amount of the aqueous formulation of the present invention will necessarily vary depending on the particular condition to be treated, the age and medical condition of the patent to be treated, the severity of the condition and like factors. Typically, the unit dosage amount of the present formulation sufficient to effect decongestion can range from about 0.01 ml to about 0.5 ml of the topical decongenstant composition. The frequency of administration of the topical composition may be vary from once up to about 10 times daily, preferably from 3 times to 6 times daily.

Another embodiment of the invention provides the present compositions in combination with a dispenser containing means for topical application of the composition to the nasal passages and sinuses, or bronchial passages and lungs. Preferred dispensers useful in such a combination include those containing spray means or inhalation means. However, dispensers containing dropper means for topically applying the liquid compositions as nose drops to the nasal passages may also be used.

Dispensers containing spray means are useful for topically applying a spray of liquid droplets directly to nasal passages. Such dispensers are well-known and generally consist of flexible plastic containers having a spray nozzle fixedly attached thereto. The spray nozzle is configured for insertion into the nasal opening. Upon squeezing the container, the solution in the dispenser is forced through the nozzle and emerges as a fine spray of droplets. Other conventional dispensers with spray means such as pump sprays or aerosol sprays may be used in accordance with this embodiment of the present invention.

Dispensers containing inhalation mist means are useful for topically applying a fine mist directly to nasal passages or indirectly to bronchial passages and lungs. The fine mist provided by such inhalers can be inhaled through the nose or the mouth. Dispensers designed for inhalation of the mist through the nose are useful for topical administration of the present compositions to the nasal passages and/or bronchial passages and lungs. Inhalers designed for providing a mist to be inhaled through the mouth are useful for topical administration of the composition to bronchial passages and lungs. Various dispensers having inhalation mist means as part of or attached to the container are well-known and include plastic squeeze bottles, pump dispensers, and aerosols, for example.

The following non-limiting examples are given to further illustrate the preferred embodiments of the invention. All relative proportions are set forth as percentages by weight.

EXAMPLE 1

A decongestant composition within the scope of the present invention is prepared according to the processing procedure as particularly described hereinabove by combining the following ingredients:

| INGREDIENT | WT. PERCENT |
| --- | --- |
| Aloe vera gel | 30.00 |
| Castor oil | 15.00 |
| Sodium metasilicate | 10.00 |
| Calcium chloride | 5.00 |
| Purified water | 40.00 |

The above composition was placed in a 15 ml plastic squeeze bottle having an attached spray nozzle for insertion into the nasal opening. One-tenth ml of the composition of Example 1 is sprayed through the nozzle into each nostril of an adult patient with post-nasal drip. The patient reported that the post-nasa substantially ceased.

EXAMPLE 2

Following the procedure of Example 1, a decongestant compositions was prepared having the following ingredients in the designated proportions:

| INGREDIENT | WT. PERCENT |
| --- | --- |
| Aloe vera gel | 25.00 |
| Castor oil | 15.00 |
| Sodium metasilicate | 5.00 |
| Calcium chloride | 5.00 |
| Purified water | 50.00 |

One-fifth ml of the above composition is sprayed as a mist from an aerosol dispenser into the mouth of an adult patent with bronchial congestion. The patent reported that the congestion was substantially diminished.

It should be understood that there may be various changes and modifications of the representative embodiments herein chosen for purposes of illustration without departing from the spirit and scope of the invention. Accordingly, the foregoing illustrations are not to be interpreted as restrictive of the invention beyond that necessitated by the following claims.

I claim:

1. A decongestant composition for treatment of symptoms associated with respiratory diseases consisting essentially of 20 to 35% by weight of aloe vera, 5-15% castor oil, 5-10% sodium metasilicate, 5-10% and calcium chloride as the active ingredients, and 30 to 65% by weight of purified water to form an aqueous solution.

2. The composition according to claim 1 wherein said aqueous solution consists of the following formulation:

| INGREDIENT | WT. PERCENT |
| --- | --- |
| Aloe vera gel | 30.00 |
| Castor oil | 15.00 |
| Sodium metasilicate | 10.00 |
| Calcium chloride | 5.00 |
| Purified water | 40.00 |

3. The composition according to claim 1 wherein said aqueous solution consists of the following formulation:

| INGREDIENT | WT. PERCENT |
| --- | --- |
| Aloe vera gel | 25.00 |
| Castor oil | 15.00 |
| Sodium metasilicate | 5.00 |
| Calcium chloride | 5.00 |
| Purified water | 50.00 |

4. A method of treatment of symptoms associated with respiratory diseases in a human comprising topical administration to the nasal or bronchial passages of a human in need of such treatment of a safe and effective amount of a composition consisting essentially of 20 to 30% by weight of aloe vera, 10–20% castor oil, 5–10% sodium metasilicate, 5–10% and calcium chloride as the active ingredients, and 30 to 60% by weight of purified water to form an aqueous solution.

5. The method according to claim 4 Wherein the composition is administered in a unit dosage amount of about 0.01 ml to about 0.5 ml.

6. The method according to claim 4 wherein the composition is administered at a frequency of from once up to about 10 times daily.

7. The method according to claim 4 wherein the composition is administered intranasally from a dispenser having spray means.

8. The method according to claim 4 wherein the composition is administered orally from a dispenser having inhalation mist means.

* * * * *